United States Patent
Ishmael

(10) Patent No.: US 10,016,347 B2
(45) Date of Patent: Jul. 10, 2018

(54) HAIR-CONDITIONING MASK

(71) Applicant: Niucoco Inc., Cowansville (CA)

(72) Inventor: Nadeeza Yasmine Ishmael, Montreal (CA)

(73) Assignee: Niucoco Inc., Cowansville (CA)

( * ) Notice: Subject to any disclaimer, the term of this patent is extended or adjusted under 35 U.S.C. 154(b) by 0 days.

(21) Appl. No.: 15/347,345

(22) Filed: Nov. 9, 2016

(65) Prior Publication Data

US 2017/0128331 A1 May 11, 2017

Related U.S. Application Data

(60) Provisional application No. 62/253,453, filed on Nov. 10, 2015.

(51) Int. Cl.

| | |
|---|---|
| *A61K 8/26* | (2006.01) |
| *A61K 8/34* | (2006.01) |
| *A61K 8/362* | (2006.01) |
| *A61K 8/365* | (2006.01) |
| *A61K 8/368* | (2006.01) |
| *A61K 8/37* | (2006.01) |
| *A61K 8/06* | (2006.01) |
| *A61K 8/49* | (2006.01) |
| *A61K 8/73* | (2006.01) |
| *A61K 8/92* | (2006.01) |
| *A61K 8/97* | (2017.01) |
| *A61K 8/42* | (2006.01) |
| *A61Q 5/02* | (2006.01) |
| *A61Q 5/12* | (2006.01) |

(52) U.S. Cl.
CPC ............... *A61K 8/26* (2013.01); *A61K 8/06* (2013.01); *A61K 8/342* (2013.01); *A61K 8/345* (2013.01); *A61K 8/362* (2013.01); *A61K 8/365* (2013.01); *A61K 8/368* (2013.01); *A61K 8/37* (2013.01); *A61K 8/375* (2013.01); *A61K 8/42* (2013.01); *A61K 8/498* (2013.01); *A61K 8/73* (2013.01); *A61K 8/922* (2013.01); *A61K 8/97* (2013.01); *A61Q 5/02* (2013.01); *A61Q 5/12* (2013.01); *A61K 2800/48* (2013.01); *A61K 2800/524* (2013.01)

(58) Field of Classification Search
None
See application file for complete search history.

(56) References Cited

U.S. PATENT DOCUMENTS

| | | | | |
|---|---|---|---|---|
| 4,640,932 | A * | 2/1987 | Fong | A61K 8/0212 514/714 |
| 5,720,949 | A * | 2/1998 | Davis | A61K 8/0212 424/400 |
| 6,231,877 | B1 * | 5/2001 | Vacher | A61K 8/315 424/401 |
| 6,509,023 | B1 * | 1/2003 | Branland | A61K 8/585 424/401 |
| 2009/0068255 | A1 * | 3/2009 | Yu | A61K 8/0212 424/450 |
| 2013/0029917 | A1 * | 1/2013 | Dal Farra | A61K 8/97 514/18.8 |

FOREIGN PATENT DOCUMENTS

WO   WO 2012/058722 A1 *   5/2012   ............. A61K 36/48

* cited by examiner

*Primary Examiner* — Aradhana Sasan
(74) *Attorney, Agent, or Firm* — McAndrews, Held & Malloy, Ltd.

(57) ABSTRACT

A hair mask composition, comprising, about 50-60% of distilled water to comprise an aqueous solution, an amount of clay sufficient to produce a paste, an amount of a moisturizer component effective for adding moisture to hair strands without leaving a greasy film on hair after shampoo, and an amount of plant protein which also acts as a strengthening hair agent.

8 Claims, No Drawings

HAIR-CONDITIONING MASK

RELATED APPLICATIONS

This application is related to, and claims priority to, U.S. Provisional Application No. 62/253,453, filed Nov. 10, 2015, titled "Hair-Conditioning Mask," the complete subject matter and contents of which are incorporated herein by reference in their entirety.

FIELD OF THE INVENTION

The field of the invention is beauty and cosmetic personal care compositions or products, specifically, hair masks.

BACKGROUND OF THE INVENTION

Dry, damaged hair is a challenge many individuals struggle with today. Dry hair and damaged hair can occur due to several factors including weather exposure (e.g. both natural and severe wind and sun), mechanical treatments (e.g. brushing hair), excessive treatments using chemicals, dying hair, heat styling, etc. In combination, using cleansing products that can be excessively stripping of hair's natural oils, can also lead to split ends, dull hair, and exacerbate dry hair. To mitigate the damage, oil treatments, hair masks, and chemical treatments are commonly used.

The popularity and usage of oils for dry hair treatment has increased due to their effectiveness and simplicity. Commonly used oils include olive oil, mineral oil, avocado oil, apricot kernel oil, rice bran oil, and coconut oil. However, one problem is that, effects are usually seen after more than several hours (e.g. 8 hours) of treatment and several treatments are usually required, making it time consuming and labor intensive.

Individuals desire a treatment for hair or damaged hair that is not time consuming and labor intensive to use.

SUMMARY OF THE INVENTION

Most available hair masks are mainly comprised of silicones and/or refined oils, which may offer some cosmetic effects. But, an increasing number of consumers are looking for safer, naturally derived, non-toxic personal care products. This includes products whose ingredients are free of parabens, phthalates, sulfates, artificial fragrances and colors.

Another problem is that other available hair treatments may constitute a chemical treatment and/or may require a heating step which can further damage hair strands.

We have found that the application to hair of an aqueous solution containing a natural clay, kaolin clay, moisturizes and softens the hair strands and also promotes a natural detoxifying effect. Kaolin clay has excellent absorbent properties which can draw out impurities thus detoxifying the hair of excess oil, dirt, and pollution.

In an aspect, the invention discloses a hair-conditioning mask, comprised of naturally derived, vegan, and gluten free ingredients including kaolin clay, used to moisturize and soften dry, damaged hair strands providing both immediate and long lasting results.

DETAILED DESCRIPTION OF THE INVENTION

In all embodiments of the present composition, all percentages are by weight of the total composition, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity.

All percentages are calculated by weight unless otherwise indicated. All percentages are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

In an embodiment, the composition is an aqueous clay-based paste containing kaolin, and is comprised of a moisturizing component, a hydrolyzed plant protein, and extracts to promote healthy hair.

In another embodiment, the composition comprises, kaolin clay, active ingredients, emollients, an emulsifier system, a natural fragrance, and a preservative system.

The composition or mask may be removed with a standard cleansing shampoo.

Kaolin clay is made up of the constituent kaolinite, primarily composed of aluminum oxide ($Al_2O_3$) and silica ($SiO_2$). It is used in a variety of products including toothpaste, paper, lightbulbs, and cosmetics. In the field of cosmetics, kaolin can be found more popularly in makeup and facial masks. In facial masks, the kaolin clay draws dirt and toxins out of the pores but may cause adverse effects on the skin such as drying and flakiness.

Kaolin is high in silica and is understood to support healthy hair, strengthening hair and adding moisture. It is understood that silica promotes the connective tissue responsible for healthy hair. And, it is predicted that the clay interacts with the hair strands to promote moisturizing and softening of the hair strands.

In an embodiment, the consistency of the paste is primarily defined by the amount of kaolin used in the composition. More than 5% of kaolin has to be used otherwise the moisturizing and softening effects on hair are not apparent. Preferably, 15-25% of kaolin clay should be used. Specifically, kaolin is used as opposed to other clays because it is known to be the gentlest of clays on the market and for this reason is most beneficial in repairing dry, dull hair.

The active ingredients used in this composition are pea protein and a combination of plant extracts.

Pea protein is a reconstruction agent for hair. This particular pea protein is hydrolyzed with molecular weights equal to or less than 2,000 Daltons. The hydrolyzed protein is used to coat damaged strands as small molecular weight proteins will deposit into cuticle gaps to fill in missing and/or broken sections of the hair strands. It is important to note that the present invention uses only vegan, gluten-free, and naturally derived ingredients. Therefore, no synthetic protein, no animal proteins, nor proteins derived from wheat, barley, rye, or oat are used. Since this invention focuses primarily on moisturizing and softening hair strands, we keep the percentage of protein lower than what a typical reconstruction mask would use; it is preferred that 0.1-5% of hydrolyzed protein is used. Specifically, this invention uses hydrolyzed pea protein (*Pisum sativum*) because of its increasing attention in the cosmetic market due to its benefits as described above. Other vegetable proteins which may be used include jojoba proteins, rice proteins, and *quinoa* proteins.

Extracts known for its strengthening properties for hair are used. These include but are not limited to: *Cocos Nucifera* (Coconut) Fruit Extract, *Bambusa Vulgaris* Extract (Bamboo Extract), *Equisetum Arvense* Extract (Horsetail Extract), *Citrullus lanatus* (Watermelon) Fruit Extract, *Cymidium Grandiflorum* (Orchid) Flower Extract, *Camellia Sinensis* (Green Tea) Extract, *Rosmarinus Officinalis* (Rosemary) Leaf Extract. These extracts all act to promote healthy hair in terms of structure and moisture. A preferred range of each extract is between 0.1%-1.5%.

Further adding to the moisturizing component is a combination of two emollients. The first emollient is extra virgin coconut oil. It is preferable to use only cold pressed extra virgin coconut oil as it contains a high amount of lauric acid. Lauric acid has a small molecular structure which allows it to penetrate into the cortex of the hair, helping to moisturize and strengthen the strands. Other oils have large molecular structures and cannot easily pass through the hair cuticle. These other oils coat the hair shaft, sometimes causing a heavy, greasy feeling on the hair. Since the composition is to be a safe, non-toxic product, refined oil is not used because it uses a chemical distillation method, or is expeller pressed using added heat and is also bleached and deodorized using additional chemicals. A preferred range is 2-7% of cold pressed extra virgin coconut oil.

The second emollient is cetearyl alcohol which helps to soften hair and smooth the cuticles. It is a multi-functional ingredient because it also acts as a thickener for the composition or product and forms a creamy base. The ideal consistency of the composition or product is thick enough to coat the hair strands but thin enough so that it can easily glide onto the hair strands without flaking off. The preferred range of the cetearyl alcohol is 0.5-5%. Lowering this range causes the mask to have a more liquid consistency and increasing this range causes a thicker, stiffer consistency which becomes difficult to apply onto the hair and also difficult to remove from the hair.

The emulsifier system is necessary to prevent the water phase and oil phase from separating. In this regard, water is used as a solvent in the composition to form an emulsion with the oil phase and is also used to dissolve and dilute the other ingredients comprising the composition. Two embodiments are presented that use different emulsifiers but the emulsifiers both work to prevent splitting of the phases. These two emulsifier systems will be discussed below.

A fragrance is used to enhance the smell or spa-like experience of the hair mask application. Essential oils and synthetic fragrances can be used in as desired amounts. In keeping with the non-toxic characteristic of this composition, it is preferred to use a USDA certified organic, vegan fragrance which is comprised of natural aromatics extracted in an organic vegetable oil based carrier. Because this fragrance is not synthetic, a larger volume of fragrance may be required to be within the user's aromatic preference.

A preservative system is used to prevent growth of microorganisms and prolong the product's shelf life. It is preferred to use food grade preservatives and low toxicity preservatives.

As mentioned above, two exemplary embodiments are now presented. The first exemplary embodiment is for warmer climates and does not pass freeze/thaw testing. The second exemplary embodiment is for colder climates and does pass freeze/thaw testing. Freeze/thaw testing is when the composition is frozen and thawed to determine if the product will be stable after a freeze/thaw cycle or several freeze/thaw cycles (or 3 cycles). Failing a freeze/thaw cycle is defined as when the stability of the composition fails and the composition separates.

In the second exemplary embodiment, the emulsifier system was modified and now includes an emulsion stabilizer, and, a chelant and pH adjuster was also added. Initially, guar hydroxypropyltrimonium chloride was chosen because of its compatibility with the previous emulsifier, behentrimonium methosulfate, a cationic. Unfortunately, this also failed freeze/thaw. A more potent emulsion stabilizer, xanthan gum, was chosen. However, because of its incompatibility with behentrimonium methosulfate, a different emulsifier system was developed. In this second exemplary embodiment, we use an anionic system—a combination of glyceryl stearate and sodium stearoyl lactylate. This particular combination of emulsifiers and emulsion stabilizer resolved the freeze/thaw process.

Other compatible gums could be used and a skilled person would understand that a different percentage may be necessary to achieve the ideal consistency while also taking into account the stability of the product.

Some vegetable glycerin is also used to solubilize the xanthan gum since it is not readily miscible with water. A range anywhere between 0.6-5% can be used.

The first exemplary embodiment had a preservative system that used sodium benzoate and gluconolactone. This requires a low pH to be effective but imparts stress to the second exemplary embodiment's emulsifier system. Therefore, a modified preservative system was established comprising of sodium benzoate, potassium sorbate, and sodium dehydroacetate. Both preservative systems use food grade and low toxicity preservatives.

A minor amount of sodium gluconate, a safe and natural chelant is added to prevent degradation of active ingredients and discoloration of the product. The chelant can be added to both embodiments if desired.

Since this is a mask for hair, the ideal pH should be between 4.5-6.0, as this is the hair's natural pH and allows the product to be non-irritating to the scalp. Therefore, citric acid may be used to lower the pH to this desired range and may also be used in both embodiments. In the first exemplary embodiment, after the ingredients were mixed, the gluconolactone adjusted the pH to between 4-5, so no addition of citric acid is needed.

The method to use either mask is not labor intensive; it is a quick and easy application and results are noticeable after one treatment. Specifically, the user coats the hair strands with the mask and the mask can be left on hair from 5-30 minutes; the hair strands can be wet or dry upon application. After the application is complete, the mask is easily removed by shampooing with a regular shampoo.

It is important to note that no heat is needed to accomplish results. This is considered a positive factor since addition of high heat to hair can alter the hair fibers, further damaging the hair and adds to the circle of dry, dull hair.

Also, existing clay based masks tend to flake off and are messy. This composition or mask does not flake off and is therefore easier to carry out the application of the product.

During manufacture, the ingredients are blended in multiple phases to yield a creamy paste consistency.

Exemplary Embodiment One

| Ingredients | Percent (by weight) |
| --- | --- |
| *Aloe Vera* Juice | 32 |
| Distilled Water | 28.25 |
| Kaolin | 20 |
| Coconut Oil | 5.25 |
| Cetearyl Alcohol | 5.25 |
| Organic Fragrance | 4.5 |
| Behentrimonium Methosulfate | 1.75 |
| Gluconolactone | 0.9 |
| Plant Extracts | 0.7 |
| Tocopherol | 0.6 |
| Pea Peptide | 0.5 |
| Sodium Benzoate | 0.3 |

Exemplary Embodiment Two

| Ingredients | Percent (by weight) |
| --- | --- |
| Distilled Water | 54.40 |
| Kaolin | 20.00 |
| Coconut Oil | 7.00 |
| Glyceryl Stearate | 4.20 |
| Organic Fragrance | 4.00 |
| Glycerin | 2.00 |
| Cetearyl Alcohol | 1.75 |
| Pea Peptide | 1.50 |
| Sodium Stearoyl Lactylate | 1.05 |
| Plant Extracts | 2.00 |
| Xanthan Gum | 0.60 |
| Sodium Dehydroacetate | 0.60 |
| Sodium Benzoate | 0.50 |
| Potassium Sorbate | 0.20 |
| Sodium gluconate | 0.20 |
| Citric Acid | adjust final pH of product to 5.0 |

The following clauses are additional description of the embodiments. Clause 1. A moisturizing hair conditioning mask comprising: about 55-65% of aloe vera leaf juice and distilled water to comprise an aqueous solution; an amount of clay sufficient to produce a paste; an amount of a moisturizer component effective to add moisture to hair strands without leaving a greasy film on hair after shampoo; and an amount of emulsifier which also acts as a conditioning agent. Clause 2. The hair treatment composition of clause 1 wherein said clay comprises kaolin clay. Clause 3. The composition of clause 2 wherein said kaolin clay is from about 15-25% of said composition. Clause 4. The composition of clause 1 wherein said moisturizer component comprises cold processed unrefined coconut oil. Clause 5. The composition of clause 4 wherein said coconut oil is 2-7% of said composition. Clause 6. The composition of clause 1 wherein said emulsifier component is 5-9% of said composition. Clause 7. The composition of clause 6 wherein said emulsifier component comprises a cationic emulsifier and a fatty alcohol component. Clause 8. The composition of clause 1 further comprising extracts derived from plants. Clause 9. The composition of clause 8 wherein said extracts is 0.1-0.7% of said total composition. Clause 10. The composition of clause 1 further comprising a hydrolyzed plant protein in a range within 0.1%-5% of said composition. Clause 11. The composition of clause 1 further comprising a fragrance component in a range of 0 to 5%. Clause 12. The composition of clause 1 further comprising an antioxidant in a range within 0.1%-1% of said composition. Clause 13. The composition of clause 1 further comprising a preservative blend in a range within 0.5%-1.5% of said composition.

The following clauses are additional description of the embodiments. Clause 1A. hair mask composition, comprising: about 50-60% of distilled water to comprise an aqueous solution; an amount of clay sufficient to produce a paste; an amount of a moisturizer component effective for adding moisture to hair strands without leaving a greasy film on hair after shampoo; and an amount of plant protein which also acts as a strengthening hair agent. Clause 2A. The composition of clause 1A wherein the clay comprises kaolin clay. Clause 3A. The composition of clause 2A wherein the kaolin clay is from about 15-25% of the composition. Clause 4A. The composition of clause 1A wherein the moisturizer component comprises cold processed unrefined coconut oil. Clause 5A. The composition of clause 4A wherein the coconut oil is 2-7% of the composition. Clause 6A. The composition of clause 1A further comprising a plant protein in a range within 0.1%-5% of the composition. Clause 7A. The composition of clause 1A further comprising extracts derived from plants. Clause 8A. The composition of clause 7A wherein the extracts is 0.1-5% of the total composition. Clause 9A. The composition of clause 1A further comprising a fragrance component in a range of 0-5%. Clause 10A. The composition of clause 1A further comprising a chelator in a range within 0.1%-1% of the composition. Clause 11A. The composition of clause 1A further comprising a preservative blend in a range within 0.5%-2% of the composition. Clause 12A. The composition of clause 1A further comprising an emulsion stabilizer in range within 0.1-0.6% of the composition. Clause 13A. The composition of clause 1A further comprising an emulsifier blend in range within 1-8% of the total composition. Clause 14A. The composition of clause 1A further comprising a thickener in range within 0.5-5% of the composition. Clause 15A. The composition of clause 1A further comprising a pH adjuster in range within pH 4.5-6.0 of the final product. Clause 16A. The composition of clause 1A further comprising a gum solubilizer in range within 0.6-5% of the composition.

While particular embodiments of the present invention have been illustrated and described, it would be obvious to those skilled in the art that various other changes and modifications can be made without departing from the scope of the invention. It is therefore intended to cover in the appended claims all such changes and modifications that are within the scope of this invention.

The invention claimed is:

1. A hair mask composition, in weight percentages, comprising:
   about 50-60% of distilled water to comprise an aqueous solution;
   about 15-25% of kaolin clay sufficient to produce a paste;
   about 2-7% of cold processed unrefined coconut oil as a moisturizer component effective for adding moisture to hair strands without leaving a greasy film on hair after shampoo;
   about 0.1%-5% of pea protein as a plant protein, the pea protein with a molecular weight less than or equal to 2,000 daltons, the pea protein for depositing into cuticle gaps to fill in missing and/or broken sections of the hair strands;
   about 0.5-5% of cetearyl alcohol as a second moisturizer component and a thickener for adding creaminess to the composition such that the composition does not flake when the composition dries after application to the hair strands;

about 0.1-0.6% of xanthan gum as an emulsion stabilizer for stabilizing the kaolin clay in the composition;

about 1-8% of an emulsifier blend, the emulsifier blend is an anionic system that comprises sodium stearoyl lactylate and glyceryl stearate, the emulsifier blend for not stripping oils from the hair and for compatibility with the emulsion stabilizer to stabilize the composition to pass at least 3 freeze/thaw cycles; and wherein, the hair composition does not include silicones, refined oils, parabens, phthalates, sulfates, artificial fragrances, and colors.

2. The composition of claim 1 further comprising extracts derived from plants in a range of 0.1-5% of the composition.

3. The composition of claim 2 further comprising a fragrance component in a range of 0-5%, and the fragrance component is comprised of aromatics extracted in a vegetable oil based carrier.

4. The composition of claim 3 further comprising a chelator in a range of 0.1%-1% of the composition, and the chelator is sodium gluconate.

5. The composition of claim 4 further comprising a preservative blend in a range of 0.5%-2% of the composition, and the preservative blend comprises sodium dehydroacetate, sodium benzoate, and potassium sorbate.

6. The composition of claim 5 further comprising a pH adjuster in a range within pH 4.5-6.0 of the composition, and the pH adjuster is citric acid.

7. The composition of claim 6 further comprising a gum solubilizer in a range within 0.6-5% of the composition, and the gum solubilizer is glycerin.

8. A hair mask composition, in weight percentages, consisting of:

| | |
|---|---|
| Distilled Water | 54.40; |
| Kaolin | 20.00; |
| Coconut Oil | 7.00; |
| Glyceryl Stearate | 4.20; |
| Organic Fragrance | 4.00; |
| Glycerin | 2.00; |
| Cetearyl Alcohol | 1.75; |
| Pea Peptide | 1.50; |
| Sodium Stearoyl Lactylate | 1.05; |
| Plant Extracts | 2.00; |
| Xanthan Gum | 0.60; |
| Sodium Dehydroacetate | 0.60; |
| Sodium Benzoate | 0.50; |
| Potassium Sorbate | 0.20; |
| Sodium gluconate | 0.20; and |
| Citric Acid in an amount for adjusting final pH of the composition to 5.0. | |

* * * * *